United States Patent
Lindman et al.

(10) Patent No.: US 10,943,695 B2
(45) Date of Patent: Mar. 9, 2021

(54) SENSOR MODULE FOR PERSONAL PERFORMANCE MONITORING AND RELATED ARRANGEMENT AND METHOD

(71) Applicant: Suunto Oy, Vantaa (FI)

(72) Inventors: Erik Lindman, Vantaa (FI); Ville Mattila, Vantaa (FI)

(73) Assignee: Suunto Oy, Vantaa, FL (US)

( * ) Notice: Subject to any disclaimer, the term of this patent is extended or adjusted under 35 U.S.C. 154(b) by 0 days.

(21) Appl. No.: 15/992,225

(22) Filed: May 30, 2018

(65) Prior Publication Data

US 2018/0345079 A1    Dec. 6, 2018

(30) Foreign Application Priority Data

Jun. 2, 2017  (FI) ...................................... 20175497
Jun. 2, 2017  (GB) ...................................... 1708821

(51) Int. Cl.
*G16H 40/67*       (2018.01)
*A63B 24/00*       (2006.01)
(Continued)

(52) U.S. Cl.
CPC ............. *G16H 40/67* (2018.01); *A41D 1/089* (2018.01); *A61B 5/0022* (2013.01);
(Continued)

(58) Field of Classification Search
CPC . A63B 24/0062; A63B 60/46; A63B 71/0622; A63B 69/18; A63B 69/36; A63B 69/38; A63B 2220/12; A63B 2220/40; A63B 2220/56; A63B 2220/803; A63B 2220/807; A63B 2220/833; A63B 2225/15; A63B 2225/50; A63B 2225/54; A63B 2230/04; A61B 90/98; A61B 5/0022; A61B 5/0402; A61B 5/0488; A61B 5/1123; A61B 5/6804; A61B 5/6895; A61B 2562/0219; A41D 1/002; A41D 1/089; A41D 2600/10; A41D 13/0015; A41D 13/1281; H04Q 9/00; H04Q 2209/00; H04Q 2209/40; H04Q 2209/47; H04Q 2209/80; H04Q 2209/82;
(Continued)

(56) References Cited

U.S. PATENT DOCUMENTS 7,886,471 B2 *   2/2011   Glock ................... F41A 17/066
                                              42/70.01
8,156,545 B2 *   4/2012   Shintani ................ H04N 7/163
                                              726/4
(Continued)

FOREIGN PATENT DOCUMENTS

EP       2687114 A2     1/2014
EP       2779003 A2     9/2014
GB       2521715 A      7/2015

*Primary Examiner* — Franklin D Balseca
(74) *Attorney, Agent, or Firm* — Laine IP Oy (57) ABSTRACT

The invention relates to a sensor apparatus, comprising: a sensor unit, a wireless communication unit configured to directly or indirectly transmit and receive data to and from an external source, and means for receiving identification information from a sports item while being attached to the sports item, wherein the apparatus is initiate identification of the sports item in response to a trigger from an identification activation element in the sports item.

20 Claims, 7 Drawing Sheets

(51) Int. Cl.
| | |
|---|---|
| *A61B 5/0488* | (2006.01) |
| *A61B 5/00* | (2006.01) |
| *A61B 5/0402* | (2006.01) |
| *A61B 5/11* | (2006.01) |
| *A61B 90/98* | (2016.01) |
| *A63B 60/46* | (2015.01) |
| *A41D 1/089* | (2018.01) |
| *A63B 71/06* | (2006.01) |
| *H04W 12/06* | (2021.01) |
| *H04Q 9/00* | (2006.01) |
| *H04W 12/00* | (2021.01) |
| *A41D 1/00* | (2018.01) |
| *A63B 69/18* | (2006.01) |
| *A63B 69/38* | (2006.01) |
| *A63B 69/36* | (2006.01) |
| *G06K 19/02* | (2006.01) |
| *A41D 13/12* | (2006.01) |
| *A41D 13/00* | (2006.01) |
| *H04W 84/20* | (2009.01) |
| *G06K 19/07* | (2006.01) |
| *G06K 19/077* | (2006.01) |

(52) U.S. Cl.
CPC .......... *A61B 5/0402* (2013.01); *A61B 5/0488* (2013.01); *A61B 5/1123* (2013.01); *A61B 5/6804* (2013.01); *A61B 5/6895* (2013.01); *A61B 90/98* (2016.02); *A63B 24/0062* (2013.01); *A63B 60/46* (2015.10); *A63B 71/0622* (2013.01); *H04Q 9/00* (2013.01); *H04W 12/00512* (2019.01); *H04W 12/06* (2013.01); *A41D 1/002* (2013.01); *A41D 13/0015* (2013.01); *A41D 13/1281* (2013.01); *A41D 2600/10* (2013.01); *A61B 2562/0219* (2013.01); *A63B 69/18* (2013.01); *A63B 69/36* (2013.01); *A63B 69/38* (2013.01); *A63B 2220/12* (2013.01); *A63B 2220/40* (2013.01); *A63B 2220/56* (2013.01); *A63B 2220/803* (2013.01); *A63B 2220/807* (2013.01); *A63B 2220/833* (2013.01); *A63B 2225/15* (2013.01); *A63B 2225/50* (2013.01); *A63B 2225/54* (2013.01); *A63B 2230/04* (2013.01); *G06K 19/027* (2013.01); *G06K 19/0716* (2013.01); *G06K 19/07758* (2013.01); *H04Q 2209/40* (2013.01); *H04Q 2209/47* (2013.01); *H04Q 2209/82* (2013.01); *H04W 84/20* (2013.01)

(58) Field of Classification Search
CPC ........... H04W 12/06; H04W 12/00512; H04W 84/20; G16H 40/67; G06K 19/027; G06K 19/0716; G06K 19/07758
See application file for complete search history.

(56) References Cited

U.S. PATENT DOCUMENTS

| | | | |
|---|---|---|---|
| 9,050,001 B2 * | 6/2015 | Kassem | A61B 5/031 |
| 9,460,604 B1 | 10/2016 | Daniel et al. | |
| 9,468,835 B2 * | 10/2016 | Martikka | A63B 71/06 |
| 2006/0030781 A1 * | 2/2006 | Shennib | A61B 5/0402 |
| | | | 600/509 |
| 2006/0223634 A1 * | 10/2006 | Feldman | A63B 21/0023 |
| | | | 463/36 |
| 2011/0197006 A1 * | 8/2011 | Li | H04M 1/0254 |
| | | | 710/301 |
| 2013/0241696 A1 | 9/2013 | Fabrizio | |
| 2014/0213382 A1 | 7/2014 | Kang et al. | |
| 2015/0182841 A1 | 7/2015 | Martikka et al. | |
| 2016/0146643 A1 | 5/2016 | Martin et al. | |
| 2016/0158599 A1 | 6/2016 | Roslyakov | |
| 2016/0202779 A1 * | 7/2016 | Jiang | G06F 3/03547 |
| | | | 455/566 |
| 2016/0296810 A1 | 10/2016 | Mandel et al. | |
| 2016/0303426 A1 | 10/2016 | Martikka et al. | |
| 2018/0367674 A1 * | 12/2018 | Schalk-Schupp | H04M 9/082 |

* cited by examiner

SENSOR MODULE FOR PERSONAL PERFORMANCE MONITORING AND RELATED ARRANGEMENT AND METHOD

FIELD OF THE INVENTION

The invention relates to devices used in personal performance monitoring during sports acts, for example. In particular, the invention relates to a sensor module connectable to a sports item. The invention also relates to a sports item identification apparatus and a method.

BACKGROUND OF THE INVENTION

It is well known to measure electromyographic (EMG) or electrocardiographic (ECG) signals from different parts of a human body during sports performances, the most common example being heart beat measurement using a surface ECG sensor-containing heart beat belt with a wireless transmitter module for communicating with a monitoring device, such as a sports watch. EMG signals can be measured also from other parts of the body to monitor muscle activity in legs, arms, middle body or torso, for example. Such measurements can be carried using sensors for example integrated into sports garment. It is also known to integrate signal transmitter modules into the belt or garment or to provide the module as a snap-on module to an assembly zone on the garment or belt. The module can be removed for washing the garment, for example.

US20150182841 discloses a sensor module, which is capable of distinguishing the place of mounting thereof so that it may adapt its internal operation accordingly, and a sports system or arrangement comprising such sensor module and a sports item with a mounting zone capable of indicating its identifier to the sensor module once being mounted thereon.

SUMMARY OF THE INVENTION

The invention is defined by the features of the independent claims. Some specific embodiments are defined in the dependent claims.

According to an aspect of the present invention, there is provided a sensor apparatus, comprising: a sensor unit, a wireless communication unit configured to directly or indirectly transmit and receive data to and from an external source, and a host or master identification circuit configured to receive identification information from a sports item while being attached to the sports item, wherein the host or master identification circuit is configured to initiate identification of the sports item in response to a trigger from identification activation element in the sports item when attached to the identification activation element, the host or master identification circuit being configured to communicate with a slave identification circuit in the sports item in response to the trigger.

According to another aspect of the present invention, there is provided a sports item identification apparatus, comprising: an identification unit comprising identification information stored thereon about the sports item, a contact interface for communicating the identification information from the identification unit to a sensor apparatus connected to the contact interface, and an identification activation element for triggering identification of the sports item by the sensor apparatus when the identification activation element are attached to the sensor apparatus, wherein the identification unit comprises a slave identification circuit configured to communicate with a master identification circuit of the sensor apparatus after a trigger by the identification activation element.

According to a still further aspect of the present invention, there is provided a method for facilitating monitoring of physical performance of a person, comprising detecting, by a sensor module, a trigger from an identification activation element in a sports item when the identification activation element are connected to the sensor module, initiating identification of the sports item in response to the trigger, wherein a host or master identification circuit in the sensor module is caused in response to the trigger to communicate with a slave identification circuit in the sports item, adapting internal operation of the sensor module on the basis of an identifier received from the sports item, and measuring performance-related parameters on the basis of a signal from the sports item.

According to an embodiment, at least one switch is applied to connect the host identification circuit to the slave identification circuit.

According to an embodiment, a set of data processing instructions corresponding to different identifiers is stored, and data processing instructions are selected from the set of data processing instructions on the basis of an identifier received from the sports item.

Next, embodiments of the invention and advantages thereof are described in more detail with reference to the attached drawings.

DETAILED DESCRIPTION OF EMBODIMENTS

Definitions

The term "sports item" covers various pieces of garment and other items used when performing sports. In particular, the term covers personal clothing and other wearable items, such as heart rate belts, and personal sports equipment in direct possession of the person performing the sport. The term also covers other sports items that are at least temporarily in the vicinity of the person during the performance, i.e., can join the personal-area network of a central unit (monitoring unit) of the person. An example of such item is a golf bag. Further examples are given in the detailed description. "Sports" should be taken broadly to cover all kinds of physical activities.

"Mounting zone" is zone on a sports item dedicated or at least suitable for a sensor module according to the invention. A mounting zone comprises both physical and electronic connection means for the sensor module to both remain attached to the sports item and to be able to electrically communicate with one or more sensors and/or actuators therein.

"ID" or "identifier" in a sports item is a piece of machine-readable data which indicates the type of the sports item in particular in respect of number and type(s) of sensor(s) and/or actuator(s) therein for allowing a sensor module attached to the mounting zone to utilize them. The identifier can be coded in any suitable machine-readable format encoding a specific value. Therefore, references to the "identifier" can be considered as references to the "value of identifier", where applicable. The identifier can for example be a sequence of characters bit-encoded and stored in a semiconductor memory unit.

"Processing instructions" means computer-readable code (typically arranged in a single data file) with data content, which can be interpreted by the sensor module to change its operation to correspond with the requirements of a sports item with a specific ID. The instructions may have effect for example on
- sensor signal (input signal) processing characteristics (e.g. amplification characteristics) of the module,
- actuator control signal (output signal) processing characteristics,
- internal sensor or actuator data processing algorithms,
- data interface specifications with a sensor and/or actuator, and/or
- wireless data communication characteristics with a monitor unit.

The processing instructions may comprise a set of configuration values (passive instructions), computer-executable code (active instructions), or both, in a suitable data structure, most commonly in one or more data file. Thus, the processing instructions are sports item specific software configuration files or applications, which can be utilized or run by the operating system (firmware) of the module.

"Monitoring" means receiving information on the performance using one or more sensors in one or more sports items through one or more sensor modules according to the invention. Monitoring is preferably carried out using a wearable monitoring unit, such as a wristop computer, but may be done also using any other computing device capable of communicating with the one or more sensor modules. One option is to use a mobile phone as the monitoring unit.

According to some embodiments, there is now provided an improved apparatus and method for sensor activation. A programmable sensor module for personal physical performance monitoring and/or facilitation may be adapted for mounting to a mounting zone on a sports item. The sensor module may comprise a sensor unit and a wireless communication unit configured to directly or indirectly transmit and receive data to and from an external source, such as a remote monitoring device.

The sensor module may be capable of operating with different types of monitoring applications, such as ECG and/or EMG measurement and movement measurement applications. Such multi-application sensor module may be configured to self-adapt its operation and processing of measurement data on the basis of identification information received from the sports item the module is currently mounted on. Thus, a single detachable sensor module is sufficient to serve for the communication and data processing needs for a large number of different kinds of sports items, provided that they comprise similar mounting zones and similarly readable identifiers. For example, the same module can be used during one training session in a heart rate belt for heart rate signal processing and transmission and in another session attached to muscle EMG sensor-containing clothing for muscle activity detection and activity signal transmission, or even a foot pod or bicycle pod for speed signal processing and transmission, to mention a completely different kind of measurement. Further, it is convenient to build distributed performance monitoring systems with sensors grouped in suitable single-sensor units and/or multi-sensor groups each serving for a particular purpose and associated with a single communications module.

The sensor module comprises means for receiving identification information from the sports item while being attached to the sports item. Furthermore, the sensor module is configured to initiate identification of the sports item in response to a trigger from an identification activation means or element of the sports item. The sensor module may be configured to detect the identification activation means in the sports item and initiate identification of the sports item in response to detecting the element. The initiation of the identification may refer to first detecting if the sports item supports identification. If the sports item does not comprise an ID and identification functionality/unit, the sensor module may enter a default operating mode, such as EMG or ECG measurement. The identification activation means may be provided by any element in the sports item causing the sensor module to initiate identification of the sports item, such as a part of an identification circuit in the sports item.

Hence, the identification by the sensor module and related functionality and unit can be activated or waken up only when the identification activation means are attached to and detected by the sensor module, enabling to save energy. Further, when the sports item is identified, the identification functionality and circuit in the sensor module and the sports item may be switched off. This enables to apply the sensor module-sports item interface and same contact terminals for measurement signal detection after identification. The functions of the sensor module may be determined only once attached to the sports item, by reading an identifier of the item and self-adapting the sensor module according to the identifier.

Figure 1:
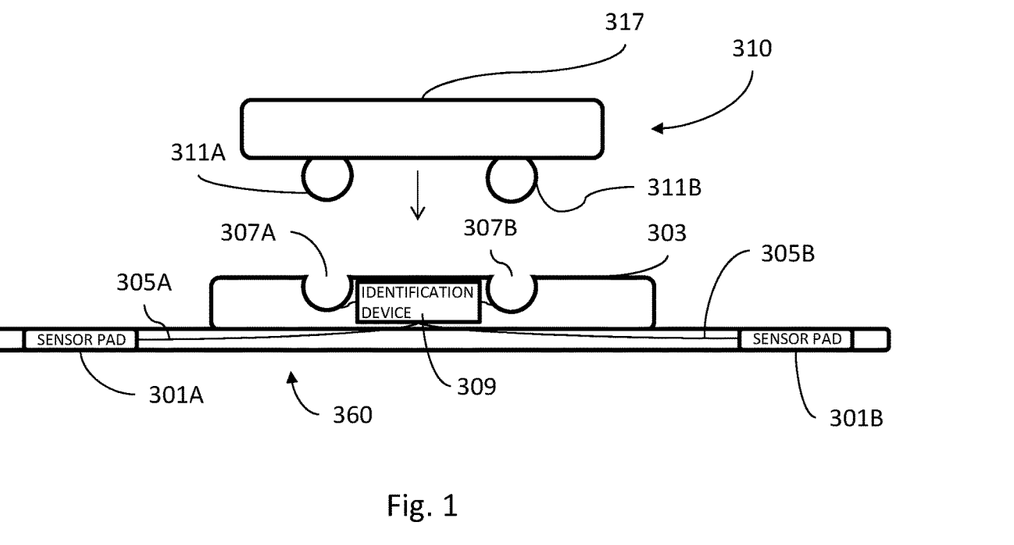
FIG. 1 shows a schematic side view of a sensor module and mounting zone on a sports item according to some embodiments of the invention.

FIG. 1 illustrates a sensor module 310 and sports item 360 according to some embodiments. The sensor module 310 comprises a housing 317 and two electric contact terminals 311A, 311B on outer surface of the housing. In this example, the contact terminals 311A, 311B are in the form of bumps or buttons capable of being snapped into suitable recess counterparts 307A, 307B of a mounting zone 303 of a sports item 360 to provide both attachment and electric connection. There may also be provided separate or additional means to take care of these functions.

The sports item 360 comprises an identification device or apparatus 309 configured to at least identify the sports item for the sensor module 310, which is to be understood broadly to refer to provision of an identifier from the sports item, which may indicate the type of the sports item and/or the measurement signal type provided by the sports item, for example. The identification device 309 may comprise an identification unit comprising memory storing identification information about the sports item, a contact interface for communicating the identification information from the identification unit to the sensor module 310 connected to the contact interface, and identification activation means causing a trigger to initiate identification of the sports item 360 by the sensor module when electrically connected to the sensor module. These units may be functional and implemented by circuitry, some embodiments illustrated later.

In the example of FIG. 1, the identification device 309 is electrically connected to the counterparts 307A, 307B. In this example, the counterparts 307A, 307B are additionally connected to sensor pads 301A, 301B using suitable wirings 305A, 305B in the sports item 360 to provide an EMG or ECG signal to the module 310. It is to be appreciated that there may be more than two contacts between the sports item 360 and the sensor module 310, for example in EMG measurement applications. Additional contacts may be taken into use in the sensor module 310 when needed, depending on the sports item in question.

Thus, when the module 310 is connected to the mounting zone 303, after the trigger from the sports item, it is able to connect the identification device 309 and receive the identifier stored therein. The module 310 may send commands, such as a memory read command to the identification device to read the identifier.

As an alternative to the illustrated wired sports item identifier access, the access may take place wirelessly. For example, there may be a radio-frequency identification (RFID) tag, such as a near-field communication (NFC) tag embedded in the mounting zone 360 and the module 310 contains a corresponding RFID/NFC reader unit for reading the identifier. In this case, the contact terminals of the module serve for sensor signal reading only.

If the sports item 360 contains a local processing unit for processing sensor and/or actuator data, the identification device or at least part thereof can be integral with that processing unit or memory used by the processing unit.

Figure 2:
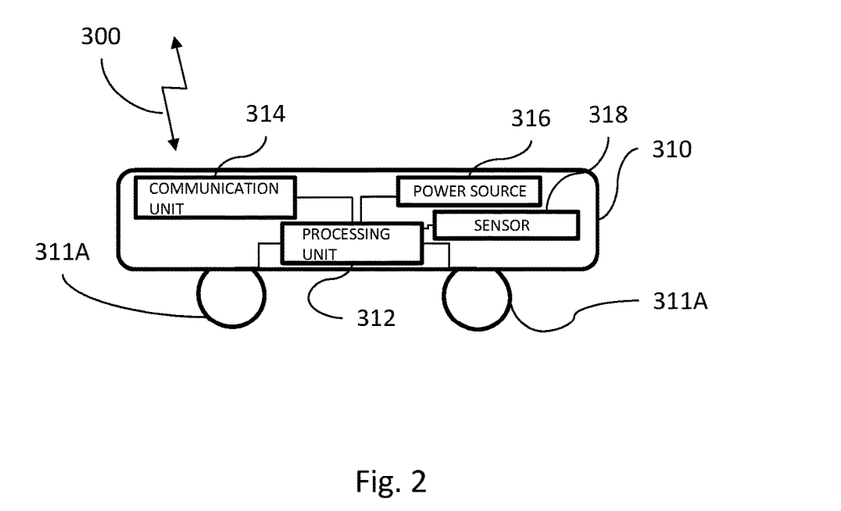
FIG. 2 shows a schematic block diagram of a sensor module according to some embodiments of the invention.

FIG. 2 illustrates main internal components of a sensor module 310 according to some embodiments. The module 310 comprises a processing unit 312 which controls and processes the input and output of the module 310 via a wireless communication unit 314 (to and from a monitoring unit) and the contact terminals 311A, 311B towards the identification device 309 in the sports item. There may provided a separate input and/or output unit (not shown) between the processing unit 312 and the contact terminals 311A, 311B, the input and/or output unit comprising necessary circuits for amplification of the input signals, if needed.

The processing unit 312 may comprise a microcontroller operated by firmware, and an amount of memory for storing i.a. processing instructions. One example of a suitable microcontroller is a Nordic Semiconductor nRF52832 comprising 32 bit ARM® Cortex®-M4 with 64 kB on-chip RAM and 512 kB on-chip FLASH, an external memory and a 128 kB EEPROM (Microchip AT24CM01) link. There may also be a separate memory circuit (not shown) for storage of larger amounts of data. Tasks of the processing unit 312 include performing internal data processing actions of the sensor module 310 and controlling communication to/from the monitoring unit and the sports item the module is attached to. The processing unit may execute processing instructions selected on the basis of the ID received from the sports item.

The communication unit 314 comprises an antenna and necessary electronics for amplification of the received and transmitted signals and for coupling with the processing unit 312. The communication unit 314 can utilize any desired wireless communication protocol. The protocol is preferably a time slot-based protocol. Examples of suitable protocols include like Bluetooth LE and ANT+, using direct-sequence spread spectrum (DSSS) modulation techniques and an adaptive isochronous network configuration, respectively. A thorough description of the necessary hardware for various implementations is available e.g. from the Texas Instrument®'s handbook "Wireless Connectivity" which includes IC circuits and related hardware configurations for protocols working in sub-1- and 2.4-GHz frequency bands, such as ANT™, Bluetooth®, Bluetooth low energy, RFID/NFC, PurePath™ Wireless audio, ZigBee®, IEEE 802.15.4, ZigBee RF4CE, 6LoWPAN, GPS.

Accordingly, the wireless communication unit 314 may transmit and receive data to and from an external source, such as a server or a terminal device or both either directly or indirectly. For example, the sensor module 310 may communicate with a server via a wireless link 300 wither directly or through a terminal device, such as a smart phone, tablet, smart watch, etc. The sensor module 310 is powered by a power source 316, most typically a battery. There are also means (not show) for charging or allowing for changing the battery. In some embodiments, the element 316 is an energy harvesting collector, employed to power the module 310 or a part thereof. For example, application of new semiconductor materials, such as new class III-V semiconductors, may enable very low current consumption.

The sensor module 310 may also include at least one sensor 318, such as EMG or ECG sensing element, a movement sensing element, or other type of sensor for personal performance or condition measurement. The sensor is functionally connected at least to the processing unit 312 and may be configured to generate measurement data on the basis of signal from the sports item and output the measurement data for the processing unit 312 for processing or for transmission to an outside processor for processing. In an embodiment, the movement sensing element comprises an accelerometer, particularly a multi-axis sensor, such as a nine-axis sensor comprising three-axis acceleration sensor, three-axis magnetic sensor, and a three-axis gyroscope, a piezoelectric element configured to deform in response to the deformation of fabric of a wearable garment during movements, a gyroscope, a magnetometer, a pressure sensor, a temperature sensor, or any combination of the aforementioned. Some other examples that the sensor module may be configured to receive include acceleration signal, power signal, speed signal, and position signal.

It is to be noted that FIG. 2 is simplified and various modifications and further elements and/or connections may be provided. For example, the sensor 318 may be directly connectable to the terminals 311A, 311B.

Figure 3A:
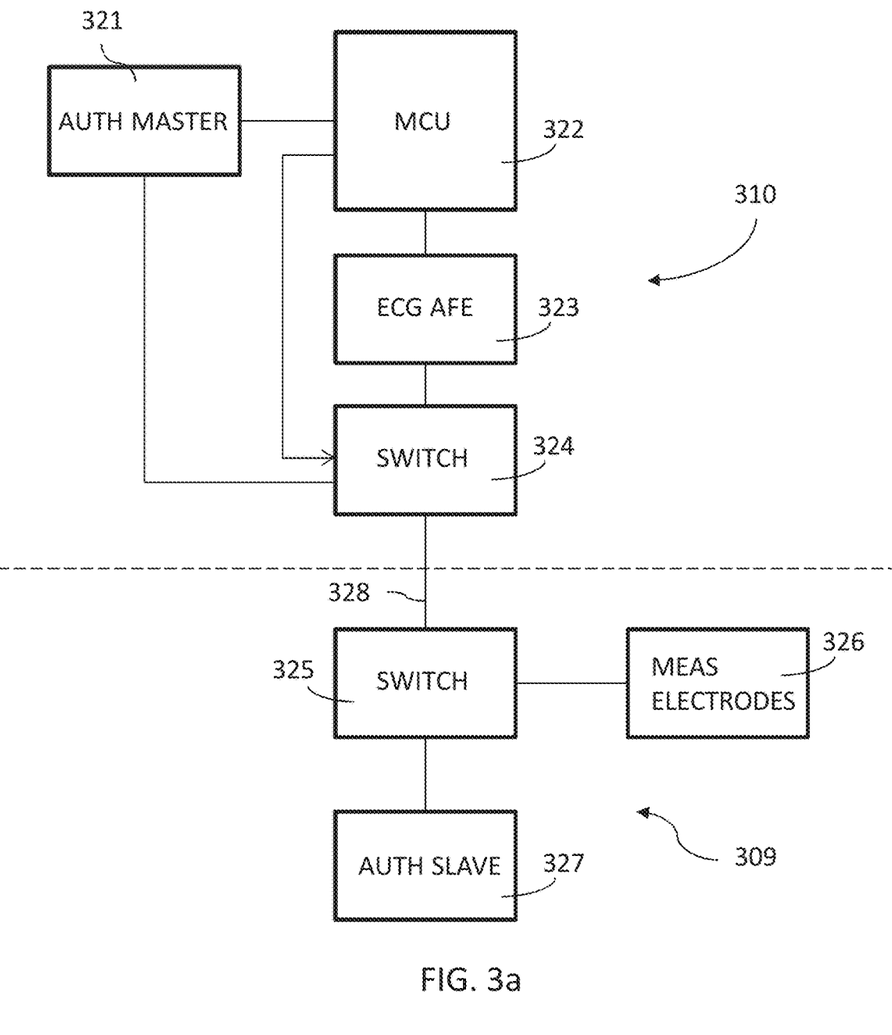
FIG. 3a illustrates elements of the sensor module and a sports item identification device according to some embodiments of the invention.

FIG. 3a illustrates further details of the sensor module 310 and the sports item identification device 309 according to some embodiments. The sensor module 310 may comprise a host or master identification or authentication circuit 321 for identifying or authenticating the sports item. The master identification circuit 321 may be caused, in response to the trigger from the sports item identification device 309, to communicate with a slave identification circuit 327 in the sports item 309 comprising the activation element. In some embodiments, the sensor module 310 and the identification 309 are configured to apply a signal from the master identification circuit 321 both for powering the slave identification circuit 327 and signalling with the slave identification circuit during the identification. For this purpose, a 1-Wire or similar system may be applied.

A microcontroller unit (MCU) 322 may comprise at least some of the features of and be configured to carry out at least some of the functions of the processing unit 312. In the example of FIG. 3a, the sensor module 310 comprises an ECG sensor, and ECG analogue front end (AFE) 323 represents measurement circuit for ECG signal received from measurement electrodes 326 of or connected to the sports item identification device 309. In such embodiments the interface 328 may comprise two terminals (not shown) from a heartrate belt or similar to the ECG AFE 323. However, it is to be appreciated that instead of, or in addition to, ECG monitoring, other sensor types may be applied in the system of FIGS. 3a and 3b.

The sensor module 310 may comprise a switch 324 controllable to connect the host identification circuit 321 to the identification device 309 and further to the slave identification circuit 327 via an interface 328. The MCU 322 may be configured to control the switch 324 to connect the master identification circuit 321 to the sports item identification device 309 in response to the trigger from the sports item identification device 309 and control initiation of the identification of the sports item by the master identification circuit 321.

In an embodiment, the processing unit 312, 322 is configured to be activated by the sensor unit 323 circuit in response to the trigger from the sports item identification device 309. The switch 324 may be configured as a default to connect the ECG AFE 323 to the sports item interface, such as the contact terminals 311A, 311B. In case of ECG applications and other applications in which the sensor is applied against skin, the sensor unit circuit and the processing unit may be configured so that small impedance caused by human body to the measurement electrodes 326 wakes up the electronics and further the processing unit 312, 322, which then initiates the identification (by the master identification circuit 321). This enables to further save power when the sensor module is not used. In response to activation of the processing unit, the processing unit may cause sensing of the presence of the activation element, e.g. by controlling the switch 324 and/or the master identification circuit 321.

The sports item device 360 identification device 309 may comprise a switch 325. The switch 325 in some embodiments may as default mode of operation connect the interface 328 to the measurement electrodes 326 and may provide the trigger for identification for the attached sensor module 310. The switch 325 is further configured to connect the contact interface 328 of the sports item 309, such as the counterparts 307A, 307B, to the slave identification unit 327 for initiating the identification of the sports item by the master identification circuit 321 of the sensor module 310. The switch 325 may be configured to cause this connection in response to a signal from the sensor module, in a further embodiment in response to a powering and communicating signal from the master identification circuit 321.

The processing unit 312, 322 is configured to cause connecting of the sensor unit 318, 323 to the contact interface 328 of the sports item (via at least one switch 324) for receiving measurement signal after identification of the sports item or in response to failing to detect or receive a response from the slave identification circuit 327. The switch 325 may be configured to connect the contact interface 328 to at least one measurement electrode 326 in response to a signal from the slave identification circuit 327 or the sensor module 310 after authentication of the sports item.

An example of interoperation of the sensor module 310 and the sports item identification device 309 according to an embodiment illustrated in connection with FIG. 3a is as follows: As the user wears a belt comprising the identification device 309, the electrodes in the belt are as default connected to the ECG AFE 323, which is configured to detect the finite impedance caused by the human body. In response to this, the MCU 322 is activated and it controls the switch 324 to a state in which the ECG measurement channel is closed and the master identification circuit 321 is connected to the identification device 309. 1-wire signalling or similar signal from the master circuit 321 powers the switch 325, which causes the switch 325 to detach the electrodes 326 and connect the interface 328 to the slave identification circuit 327. The 1-wire signal activates the slave identification circuit 327 for the identification. When the identification is completed, the 1-wire signalling ends upon which the switch 325 returns to (default) measurement and high-impedance mode. Only very small current leakage property is allowable from the switch to avoid attenuation of the low-voltage measurement signal.

Figure 3B:
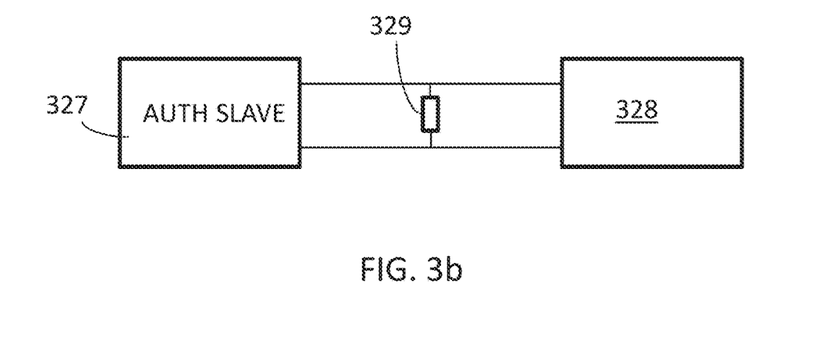
FIG. 3b illustrates a slave identification circuit arrangement according to an embodiment of the invention.

With reference to FIG. 3b, in some embodiments the identification activation means comprise at least part of a slave identification circuit comprising an actively coupled resistor 329. In an embodiment, the identification activation element is part of the slave identification circuit 327. Such embodiments enable to trigger identification at the attached sensor module in connection with sensor applications not including human body contact and electrodes. Hence, the sensor module 310 can support attachment to various different sports item and sensor types and perform identification with minimal power consumption.

Examples of currently available components that may be used for implementing the elements of FIGS. 3a and 3b include, but are not limited to: Authentication master 321: Maxim Integrated DS24L65, authentication slave 327: Maxim Integrated DS28EL15, signal switch 324: Maxim Integrated MAX4636, ECG analog front end 323: Maxim Integrated MAX30001, MAX30003 or MAX30004.

In an embodiment, the sensor module 310 is connected to a network of sensors, such as a personal area network (PAN) of sensors. The sports item 309 may comprise or be connected to a set of networked sensors. Block 326 may thus be replaced by a sensor network connected to the switch 325. An example of such wired sensor network is provided in U.S. Pat. No. 9,555,286. It is to be appreciated that FIGS. 3a and 3b illustrate just some embodiments for implementing the present functionality related to triggering identification of the sports item. For example, the switch 325 is not required if the sports item 309 does not comprise the body measurement electrodes.

A sports monitoring system may comprise the sensor module 310 and the sports item identification device 309 according to at least some of the embodiments illustrated above. Further, the system may comprise a monitoring unit capable of wirelessly communicating with the sensor module so as to receive sensor data from the sensor module.

Figure 4:
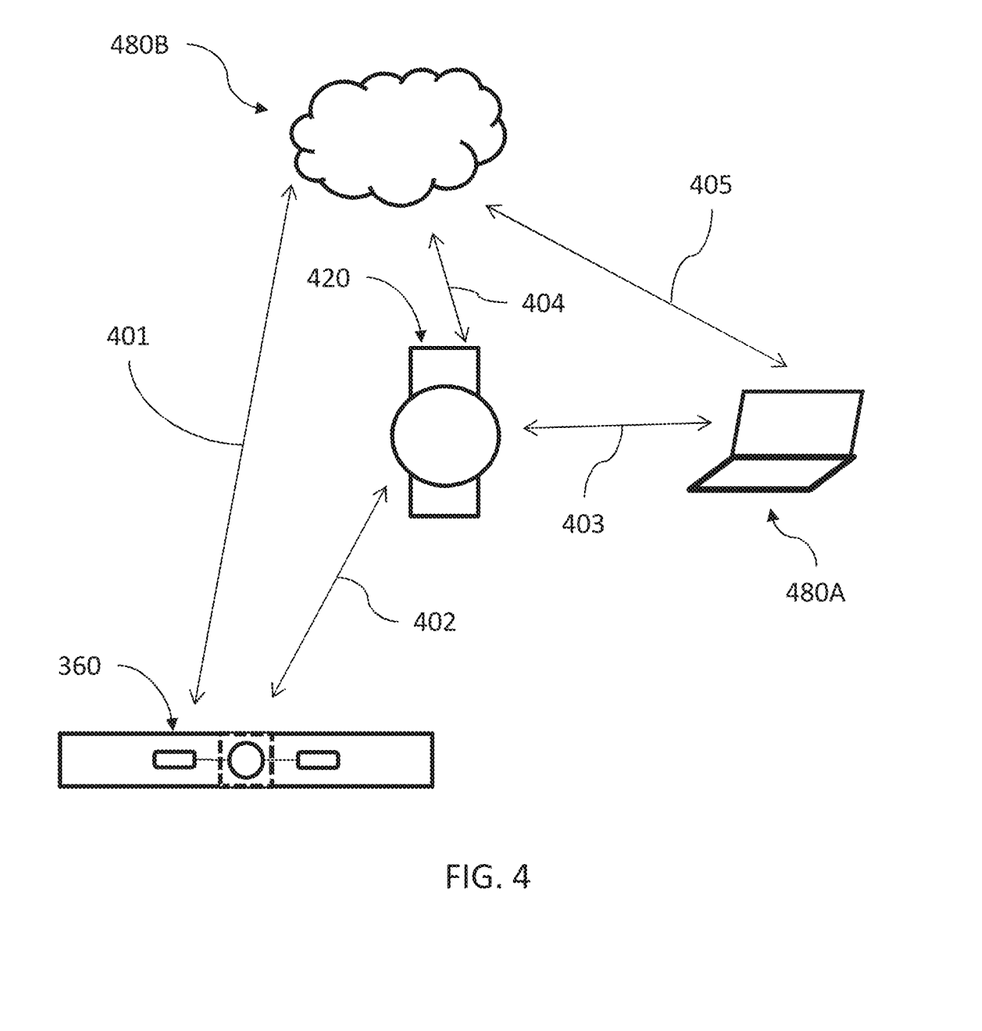
FIG. 4 illustrates a system according to an embodiment.

FIG. 4 illustrates an example of one foreseeable system. The sports item 360 may communicate with a cloud or server 480B directly via a wireless link 401 provided by the wireless communication unit 314. Alternatively, the traffic may be routed through a terminal device 420, such as a smart watch or smart phone or similar, via a wireless link 402 between the sports item 360 and the terminal device 420 and wireless link 404 between the terminal device 420 and the cloud or server 480B. Particularly, data may be delivered from the sensor module 310 first to a terminal device 420, such as a smart watch, and then directly or via a second terminal device (not shown), such as a mobile phone, to a web server 480B. In such an embodiment, the first terminal device need not be equipped with a mobile data connection to a web server. Instead, the first terminal device may perform only light processing to the measurement data, whereas the majority of the data processing and traffic to and from a web server may be carried out in a second terminal device better equipped for the task.

Also, the further processing steps and/or transmission of data may be performed at a later stage in respect to the measuring step. Furthermore, the traffic may be routed through another computing device 480A, such as a personal computer or another server via a wireless link 403 between the terminal device 420 and the computing device 480A and wireless link 405 between the computing device 480A and the cloud or server 480B. Other networks are foreseeable including replacing one or several links with wired connections.

By virtue of the wireless communication unit 314 the program controlling the sensor module 310 may be stored on a built-in memory or an external memory on an external device, such as a terminal device, e.g. a smart phone etc., or a server or cloud or similar.

Figure 5:
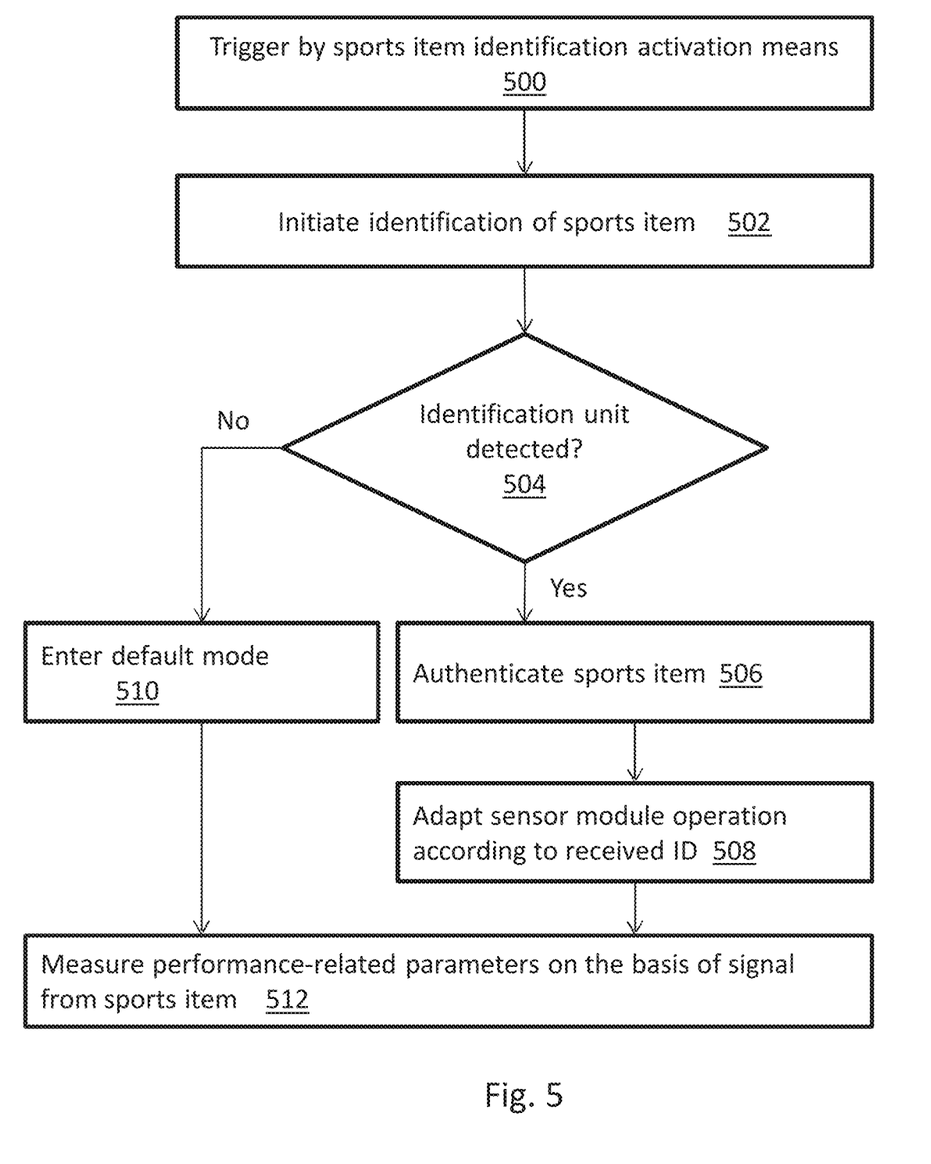
FIG. 5 shows a flow chart of the present method according to an embodiment.

FIG. 5 illustrates a method according to some embodiments. The method may be applied in the sensor module, and further by the processing unit 312, 321. The processing unit is attached to a sports item, such as the sports item 360. A trigger by identification activation means in a sports item identification device, such as the device 309 of FIGS. 1 and 3a/b, is received or detected 500. The trigger causes initiation 502 of identification of the sports item. The sports item identification device, such as the device 309 of FIGS. 1 and 3a/b, is then connected. This may be implemented by an appropriate signal which also may power the sports item identification device.

If an identification unit, which may also refer to directly detecting identification information from the identification unit, is detected in block 504, the sports item is identified or authenticated 506. Thus, an ID is received, and there may be an authentication procedure carried out. If no identification element is found, a default operating mode, such as ECG measurement may be entered 510. In an alternative embodiment, the device does not enter a measurement mode but may output an error if the sports item cannot be identified.

After authentication or identification 506 of the sports item, internal operation of the sensor module is adapted 508 according to the received ID and an operating mode associated with a received identifier may be entered 508. Data processing instructions may thus be selected from a set of data processing instructions on the basis of the identifier received from the sports item. The processing instructions may be stored in and/or provided to the sensor module as stand-alone applications, which can be run by the operating system (firmware) of the module. This allows for very generic modules still suitable for a variety of uses to be manufactured.

The sensor module and the identification apparatus can be used with any sports items within a personal-area network of a person. This includes at least all items that the person wears, holds or touches during the performance.

Figure 6A:
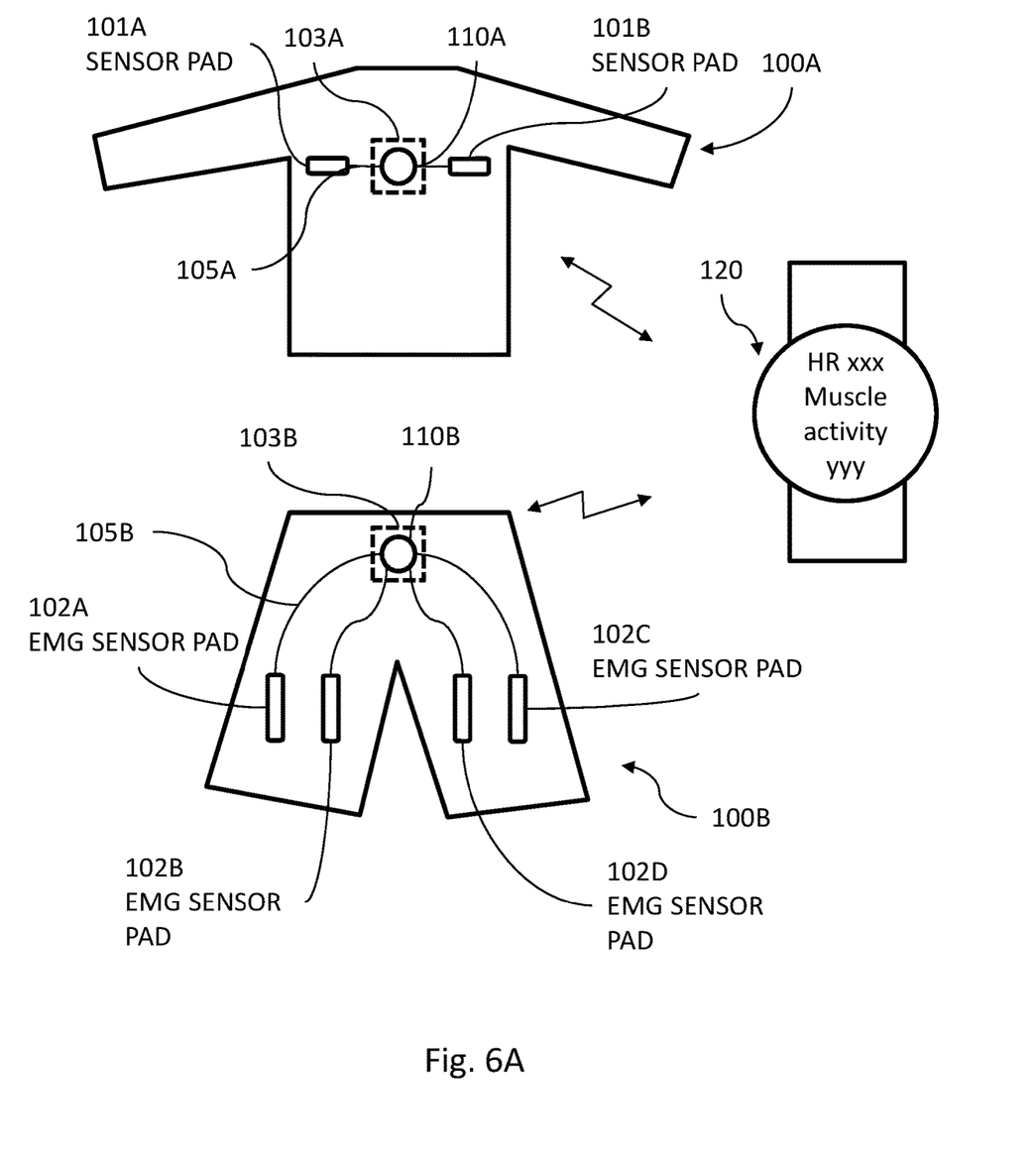
FIGS. 6A and 6B illustrate monitoring systems according to some embodiment with sensor modules attached to sports garments.

FIG. 6A shows one example of a system that can take advantage of the invention. The system comprises a first sports garment (shirt) 100A and a second sports garment (shorts) 100B, both containing integrated sensors. The shirt 100A comprises first sensor pads 101A, 101B positioned to measure heart signal. In the shorts 100B, there are second EMG sensor pads 102A-D are positioned in two groups (102A and 102B/102C and 102D) against both thighs to measure thigh muscle EMG activity. The heart ECG pads 101A, 101B are connected to a first mounting zone 103A in the shirt 100A using first wirings 105A. Similarly, the thigh muscle activity EMG pads 102A-D of the shorts 100B are connected to a second mounting zone 103B in the shorts using second wirings 105B. To the first and second mounting zones 103A, 103B, there are attached a first and a second sensor module 110A, 110B, respectively, such that they are electrically connected to the first and second wirings 105A, 105B and further to the first and second sensor pads 101A-B, 102A-D, respectively. Both mounting zones 103A, 103B comprise an identification device comprising an identifier, which are received by the sensor modules 110A, 110B to be able to adapt the sensor modules for these particular measurement environments. Thus, the modules 110A, 110B can be identical in hardware and firmware but can change their internal operating instructions to co-operate with the environment they are connected to.

There is also provided a monitoring unit (wristop computer) 120, to which the sensor modules 110A, 110B wirelessly transmit the measurement information received from the sensors after processing in the processing units of the sensor modules 110A, 100B. The monitoring unit 120 may also serve to provide the operating instructions for the modules 110A, 110B based on the identifiers read by the modules 110A, 110B upon request by the modules. The request and transmitting the instructions are preferably also done through wireless communication. Alternatively, the instructions corresponding to the identifiers may be stored in the modules 110A, 110B, whereby no communication with the monitoring unit 120 at the adaptation phase is needed.

To give an example of the adaptation of the modules, the identifier of the shirt 100A can indicate to the module 110A that there is one sensor (two pads) of ECG type connected and that the signal amplification level required is X. The identifier of the shorts 100B can indicate to the module 110B that there are two sensors (four pads) both of EMG type connected and that signal amplification level required for both of these is Y. As indicated above, the indication may take place through internal-only adaptation (instructions pre-stored in the module) or through communication with another device, such as the monitoring unit, a computer or a cloud service.

Figure 6B:
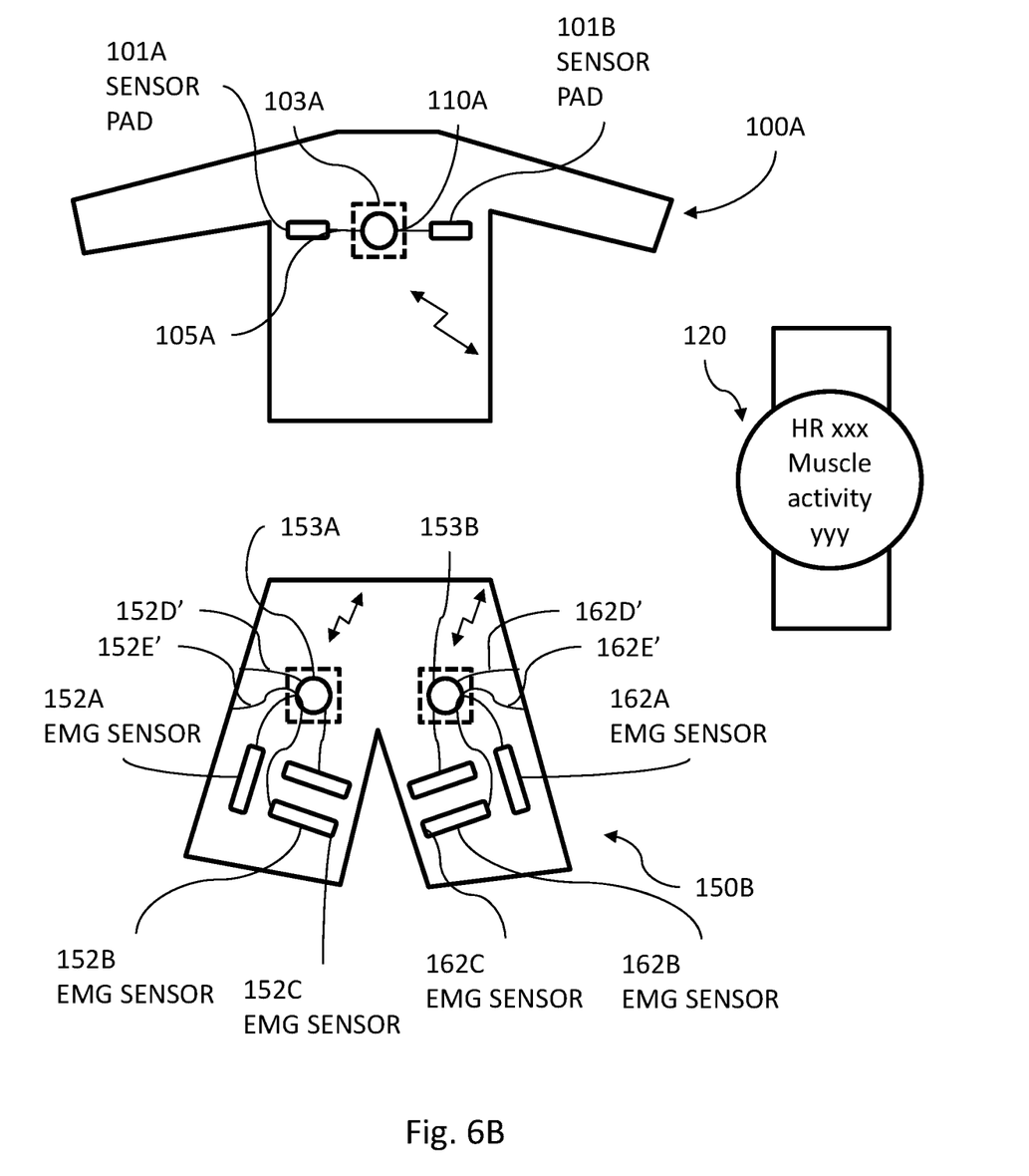

FIG. 6B illustrates a system otherwise similar to that of FIG. 1A but with the shorts 150B designed in an alternative way. The shorts 150B comprise mounting zones 153A, 153B for sensor modules separately for each leg. The mounting zones 153A, 153B are connected to EMG sensors 152A-C, 162A-C arranged on each leg, respectively. The illustrates sensors 152A-C, 162A-C are located on the front and side portions of the legs and connected to the mounting zones 153A, 153B with suitable wirings integrated to the garments but there may be one or more additional sensors (not shown) on the back sides of the legs, again connected with wirings 152D', 152E', 162D', 162E'. Thus, a complete muscular activity sensing system for each large muscle group and each leg is formed. Combined with the ECG signal from the subsystem of the shirt 100A, a comprehensive performance monitoring system is obtained.

Instead of two separate mounting zones 153A, 153B and respective identifiers therein at the pants 150B, there may be only one mounting zone or even more mounting zones. The illustrated sensor grouping is made only to exemplify the possibilities of the invention.

Figure 7:
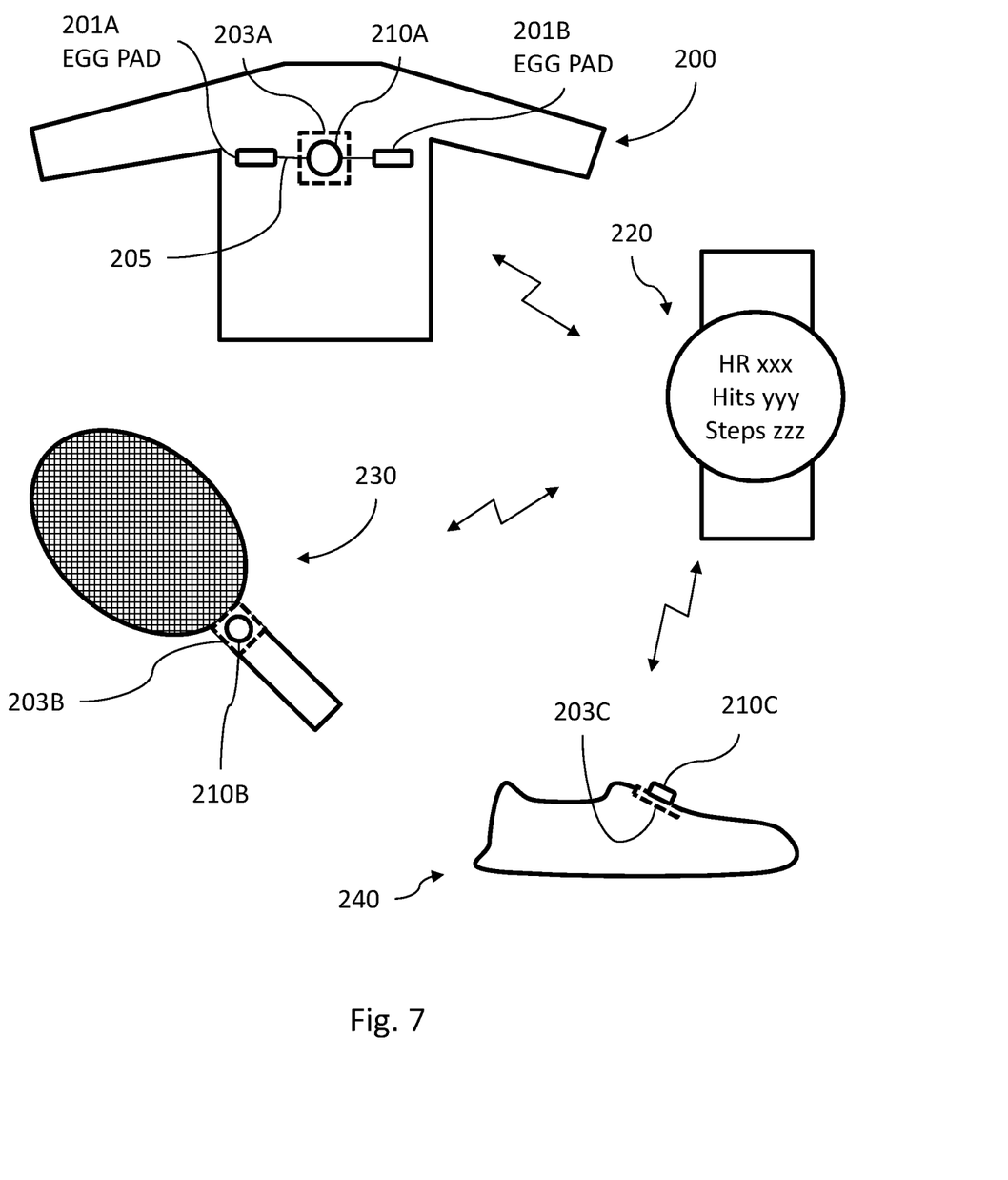
FIG. 7 shows another exemplary monitoring system with sensor modules attached to garment, tennis racket and shoe.

FIG. 7 shows a modified system example with a sports garment 200 corresponding to the garment 100A of FIG. 1A. The ECG pads are denoted with reference numerals 201A, 201B, the first mounting zone with 203A, wirings with 205 and the first sensor module attached thereto with 210A. The mounting zone 203A comprises a respective identifier readable by the module 210A.

In addition, there is provided a tennis racket 230 with a second mounting zone 203B and a second sensor module 210B and a sports shoe 240 with a third mounting zone 203C and a third sensor module 210C. The mounting zones 203B, 203C of the racket 230 and shoe 240 may be connected to acceleration sensors, orientation sensors or position sensors, to mention some examples, so as to be able to communicate corresponding acceleration, orientation or position information to the communication units 210B, 210C and further to the monitoring unit 220. The mounting zones 203B, 203C can also contain respective identifiers readable by the modules 210B, 210C to indicate what kind of operation of the sensor modules 210B, 210C are required.

It is also possible that the racket 230 and/or shoe 240 are not provided with any sensors connected to the mounting zones 203B, 203C. In that case, their identifiers may "tell" the modules 210B, 210C that an internal sensor, such as an acceleration sensor, of the modules 210B, 210C are to be used. In this case, the identifiers can also be "void". In other words, if a module is not able to find any identifier with specific data content (identifier code), it assumes by default to operate in a particular way, typically using its internal sensor and corresponding pre-stored processing instructions for usage of the internal sensor.

In the examples above, only sports items containing monitoring means functionally connectable with the sensor module are discussed for simplicity. However, the sports items and/or the sensor module may comprise also other devices and/or functionality, such as an actuator. An actuator differs from a sensor in that it produces a noticeable output for the user, whereas a sensor provides measurement information for the communication module to process and forward. The output may be visual, audible or mechanical (involving motion), for example. Examples of actuators include an integrated display or audio output device in a garment. Another example is a tactile output device.

The sensing and actuation functions typically relate to each other, but they need not do so. Sensor data analysis and actuator control can be carried out in suitable electronics of the sports item itself, but is even more preferably carried out in the present programmable sensor module, which takes input from the sensor, processes the input and controls the actuator. In the first case, only power is minimally required from the sensor module to the sensor/actuator. In the latter case, also data signals needs to be transferred between the module and the sensor/actuator, which is of course possible in the first case too.

An example of a combined device is a sensor with built-in visual or audible output of ECG/EMG signal, signal frequency or indication of target ECG/EMG activity rate (e.g.: in coaching mode: advice to increase or decrease heartbeat or intensity of training). Another example is a GPS sensor with built-in speed and/or direction indicator. A still another example is a racket, bat or club which comprises an acceleration sensor and/or gyroscope and is able to provide instant feedback for the user on the characteristics of a hit or swing.

It should be noted that the sports items 100A, 100B, 200, 230 and 240 are preferably passive, i.e., are not provided with own power source. Instead of that, the power for both identifier-reading and sensor operations is obtained from power sources contained in the sensor modules 110A, 110B, 210A, 210B and 210C.

The present modules can be used in connection with any sports items within a personal-area network of a person. Examples are pieces of garment carried out by the person, such as shirts, trousers, socks, hats, caps, footwear, handwear and belts and various pieces of sports equipment necessary for any particular sports, including rackets, bats, clubs, sticks, skis, bicycles, balls, vehicles, and bags with one or more integrated sensors or actuators.

Examples of sensors contained in sensor module and/or the sports items include the EMG, ECG, acceleration, orientation, position sensors, temperature and pressure sensors, such as air pressure sensors, tactile sensors, pressure force sensors, grip force sensors, or foot weight distribution sensors, and photosensors. Specific sensor types for the abovementioned purposes include conductive electronic potential sensors, micromechanical acceleration sensors, micromechanical gyroscopic sensors, micromechanical magnetic sensors, micromechanical pressure sensors, satellite positioning system sensors (e.g. GPS or GLONASS) and resistive and capacitive touch sensors (with optional touch position and/or touch force detection capability) and digital imaging sensors (e.g. multipixel CCD or CMOS sensors).

Specific sports item examples include heartbeat ECG belts, muscular EMG belts or garments and tennis rackets, golf clubs, skiing equipment with acceleration sensors or orientation sensors and photographic devices used during the performance.

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

References throughout this specification to one embodiment or an embodiment mean that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment. Where reference is made to a numerical value using a term such as, for example, about or substantially, the exact numerical value is also disclosed.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In the preceding description, numerous specific details are provided, such as examples of lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The verbs "to comprise" and "to include" are used in this document as open limitations that neither exclude nor require the existence of also un-recited features. The features recited in depending claims are mutually freely combinable unless otherwise explicitly stated. Furthermore, it is to be understood that the use of "a" or "an", that is, a singular form, throughout this document does not exclude a plurality.

The invention claimed is:

1. A sensor apparatus, comprising:
a sensor unit,
a wireless communication unit configured to directly or indirectly transmit and receive data to and from an external source,
a host or master identification circuit configured to receive identification information from a sports item while being attached to the sports item, and
a processing unit,
wherein the host or master identification circuit is configured to initiate identification of the sports item in response to a trigger from an identification activation element in the sports item when attached to the identification activation element, the host or master identification circuit being configured to communicate with a slave identification circuit in the sports item in response to the trigger,
the sports item does not comprise a power source and the identification activation element comprises an actively coupled resistor, and
the processing unit is configured to be activated in response to the trigger and configured to cause the host or master identification circuit to connect to the sports item.

2. The sensor apparatus of claim 1, wherein the sensor apparatus further comprises a switch controllable at least to connect the host or master identification circuit to the slave identification circuit.

3. The sensor apparatus of claim 1, further comprising memory for storing a set of data processing instructions corresponding to different identifiers, wherein the processing unit is capable of selecting data processing instructions from the set of data processing instructions based at least partially on an identifier received from the sports item.

4. The sensor apparatus of claim 1, further comprising: a switch controllable at least to connect the host or master identification circuit to the slave identification circuit and a processing unit and memory for storing a set of data processing instructions corresponding to different identifiers, wherein the processing unit is capable of selecting data processing instructions from the set of data processing instructions based at least partially on an identifier received from the sports item, wherein the processing unit is configured to cause the host or master identification circuit to connect to the sports item via the switch in response to the trigger.

5. The sensor apparatus of claim 1, wherein the processing unit is configured to be activated by sensor unit circuitry in response to the trigger, and the processing unit is configured, in response to the activation of the processing unit, to cause the host or master identification circuit to send identification related signal to the sports item.

6. The sensor apparatus of claim 1, wherein the processing unit is configured to cause connecting of the sensor unit to a contact interface of the sports item for receiving measurement signal after authentication of the sports item or in response to failing to receive a response from an identification unit in the sports item.

7. The sensor apparatus of claim 1, the sensor apparatus further comprising two or more electronic contact terminals for making an electronic contact with the sports item while being mounted thereon, and the host or master identification circuit is connectable to the two or more electronic contact terminals to supply power to and signal with the sports item.

8. The sensor apparatus of claim 1, wherein the apparatus is configured for receiving at least one of: electromyographic signal, acceleration signal, power signal, speed signal, and position signal.

9. The sensor apparatus of claim 1, wherein after identification of the sports item, the host or master identification circuit is switched off.

10. The sensor apparatus of claim 1, wherein the trigger activating the processing unit is based on an impedance caused by a human body to measurement electrodes of the sports item.

11. The sensor apparatus of claim 1, wherein the sensor apparatus is configured to connect a measurement circuit for electrocardiographic and/or electromyographic signal measurement as a default interface to the sports item.

12. A sports item identification apparatus comprising:
an identification unit comprising identification information stored thereon about a sports item,
a contact interface for communicating the identification information from the identification unit to a sensor apparatus connected to the contact interface, and
an identification activation element for triggering identification of the sports item by the sensor apparatus when the identification activation element is attached to the sensor apparatus, wherein the identification unit comprises a slave identification circuit configured to communicate with a host or master identification circuit of the sensor apparatus after a trigger by the identification activation element,
wherein the sports item does not comprise a power source, the trigger is adapted for activating a processing unit of the sensor apparatus, configured to cause the host or master identification circuit to connect to the sports item, and the identification activation element comprises an actively coupled resistor.

13. The sports item identification apparatus of claim 12, the sports item identification apparatus further comprising a switch configured to connect the contact interface to the identification unit for initiating the identification of the sports item by the host or master identification circuit of the sensor apparatus in response to connecting the sensor apparatus to the contact interface.

14. The sports item identification apparatus of claim 13, wherein the switch is configured to connect the contact interface to the identification unit in response to a signal from the host or master identification circuit and the switch is configured to connect the contact interface to at least one measurement contact after the identification of the sports item is completed.

15. The sports item identification apparatus of claim 12, wherein the sports item identification apparatus is configured for receiving at least one of: electromyographic signal, acceleration signal, power signal, speed signal, and position signal.

16. A sports item comprising a sports item identification apparatus, the sports item identification apparatus comprising:
- an identification unit comprising identification information stored thereon about the sports item
- a contact interface for communicating the identification information from the identification unit to a sensor apparatus connected to the contact interface, and
- an identification activation element for triggering identification of the sports item by the sensor apparatus when the identification activation element is attached to the sensor apparatus, wherein the identification unit comprises a slave identification circuit configured to communicate with a host or master identification circuit of the sensor apparatus after a trigger by the identification activation element,
- wherein the sports item identification apparatus does not comprise a power source, the trigger is adapted for activating a processing unit of the sensor apparatus, configured to cause the host or master identification circuit to connect to the sports item, and the identification activation element comprises an actively coupled resistor.

17. The sports item of claim 16, wherein the sports item further comprises one or more of a belt, garment and/or piece of sports equipment, with one or more integrated sensors or actuators.

18. The sports item of claim 16 wherein the sports item comprises a piece of sports equipment selected from: a bat, racket, club, ski and bicycle.

19. A sports monitoring system comprising a sensor apparatus, a sports item identification apparatus, and a monitoring unit capable of wirelessly communicating with the sensor apparatus so as to receive sensor data from the sensor apparatus, the sensor apparatus comprising:
- a sensor unit,
- a wireless communication unit configured to directly or indirectly transmit and receive data to and from an external source,
- a host or master identification circuit configured to receive identification information from a sports item while being attached to the sports item, and
- a processing unit,
- wherein the host or master identification circuit is configured to initiate identification of the sports item in response to a trigger from an identification activation element in the sports item when attached to the identification activation element, the host or master identification circuit being configured to communicate with a slave identification circuit in the sports item in response to the trigger and the processing unit is configured to be activated in response to the trigger and configured to cause the host or master identification circuit to connect to the sports item, and wherein the sports item identification apparatus comprises:
- an identification unit comprising the identification information stored thereon about the sports item,
- a contact interface for communicating the identification information from the identification unit to the sensor apparatus when connected to the contact interface, and
- the identification activation element for triggering identification of the sports item by the sensor apparatus when the identification activation element is attached to the sensor apparatus, wherein the identification unit comprises the slave identification circuit configured to communicate with the host or master identification circuit of the sensor apparatus after a trigger by the identification activation element, wherein the sports item identification apparatus does not comprise a power source, the trigger is adapted for activating the processing unit of the sensor apparatus, and the identification activation element comprises an actively coupled resistor.

20. A method for facilitating monitoring of physical performance of a person comprising:
- detecting, by a sensor module, a trigger from an identification activation element in a sports item when the identification activation element is connected to the sensor module,
- initiating identification of the sports item in response to the trigger by activating a processing unit of the sensor module which is configured to cause a host or master identification circuit in the sensor module to connect to the sports item, wherein the host or master identification circuit in the sensor module is caused in response to the trigger to communicate with a slave identification circuit in the sports item,
- adapting internal operation of the sensor module based at least partially on an identifier received from the sports item, and
- measuring performance-related parameters based on a signal from the sports item,
- wherein the sports item does not comprise a power source and the identification activation element comprises an actively coupled resistor.

* * * * *